(12) United States Patent
Schuette et al.

(10) Patent No.: US 10,561,539 B2
(45) Date of Patent: Feb. 18, 2020

(54) DUAL BONDER

(71) Applicant: Curt G. Joa, Inc., Sheboygan Falls, WI (US)

(72) Inventors: David Edward Schuette, Kiel, WI (US); Joram L. McClurg, Port Washington, WI (US); Jon Allen Pelland, Sheboygan, WI (US); Jeffrey W. Fritz, Plymouth, WI (US); Daniel A. Peterson, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 16/172,034

(22) Filed: Oct. 26, 2018

(65) Prior Publication Data

US 2019/0060132 A1 Feb. 28, 2019

Related U.S. Application Data

(63) Continuation-in-part of application No. 15/706,150, filed on Sep. 15, 2017.

(Continued)

(51) Int. Cl.
*B32B 37/00* (2006.01)
*A61F 13/15* (2006.01)
(Continued)

(52) U.S. Cl.
CPC ........ *A61F 13/15739* (2013.01); *B29C 65/08* (2013.01); *B29C 65/086* (2013.01); *B29C 66/1122* (2013.01); *B29C 66/21* (2013.01); *B29C 66/232* (2013.01); *B29C 66/431* (2013.01); *B29C 66/81427* (2013.01); *B29C 66/81433* (2013.01); *B29C 66/81435* (2013.01); *B29C 66/81465* (2013.01); *B29C 66/81469* (2013.01); *B29C 66/83511* (2013.01); *B29C 66/8432* (2013.01); *B29C 66/84121* (2013.01);
(Continued)

(58) Field of Classification Search
CPC ........ B29C 65/08; B29C 65/086; B32B 7/05; B32B 5/02; B32B 37/0046; B32B 37/0076; B32B 37/20; A61F 13/15739
USPC ...................................... 156/580.1
See application file for complete search history.

(56) References Cited

U.S. PATENT DOCUMENTS 3,993,532 A * 11/1976 McDonald ............ B29C 65/086
156/580.2
6,454,890 B1 9/2002 Couillard et al.
(Continued)

FOREIGN PATENT DOCUMENTS

EP 1344639 A2 9/2003

OTHER PUBLICATIONS

International Search Report pertaining to PCT/US17/51848, dated Dec. 1, 2017, 7 pages.

*Primary Examiner* — James D Sells
(74) *Attorney, Agent, or Firm* — Ziolkowski Patent Solutions Group, SC

(57) ABSTRACT

A system and method for producing a disposable undergarment, with the lateral edges of the undergarment bonded by means of an ultrasonic horn. When a blank is formed for an individual undergarment, the lateral edges of opposing edges of the blank will form the seam. When the edges are sealed together, a seam is formed. The individual undergarments may be later separated along the seams.

14 Claims, 10 Drawing Sheets

Related U.S. Application Data

(60) Provisional application No. 62/395,152, filed on Sep. 15, 2016.

(51) Int. Cl.
    *B29C 65/08*     (2006.01)
    *B32B 5/02*     (2006.01)
    *B32B 37/20*     (2006.01)
    *B32B 7/05*     (2019.01)
    *B29C 65/00*     (2006.01)
    *B29L 31/48*     (2006.01)

(52) U.S. Cl.
    CPC .... *B29C 66/9392* (2013.01); *B29C 66/93441* (2013.01); *B29C 66/93451* (2013.01); *B32B 5/02* (2013.01); *B32B 7/05* (2019.01); *B32B 37/0046* (2013.01); *B32B 37/0076* (2013.01); *B32B 37/20* (2013.01); *A61F 2013/15869* (2013.01); *B29C 66/8167* (2013.01); *B29L 2031/4878* (2013.01); *B32B 2310/028* (2013.01); *B32B 2555/02* (2013.01)

(56) References Cited

U.S. PATENT DOCUMENTS

| | | |
|---|---|---|
| 7,449,084 B2 | 11/2008 | Nakakado |
| 9,144,624 B2 | 9/2015 | Schneider et al. |
| 2001/0040014 A1 | 11/2001 | Green et al. |
| 2002/0017366 A1 | 2/2002 | Inagaki et al. |
| 2010/0218881 A1* | 9/2010 | Yamamoto ........ A61F 13/15739 156/73.1 |
| 2015/0298390 A1 | 10/2015 | Shimada |
| 2016/0016748 A1 | 1/2016 | Oku et al. |

* cited by examiner

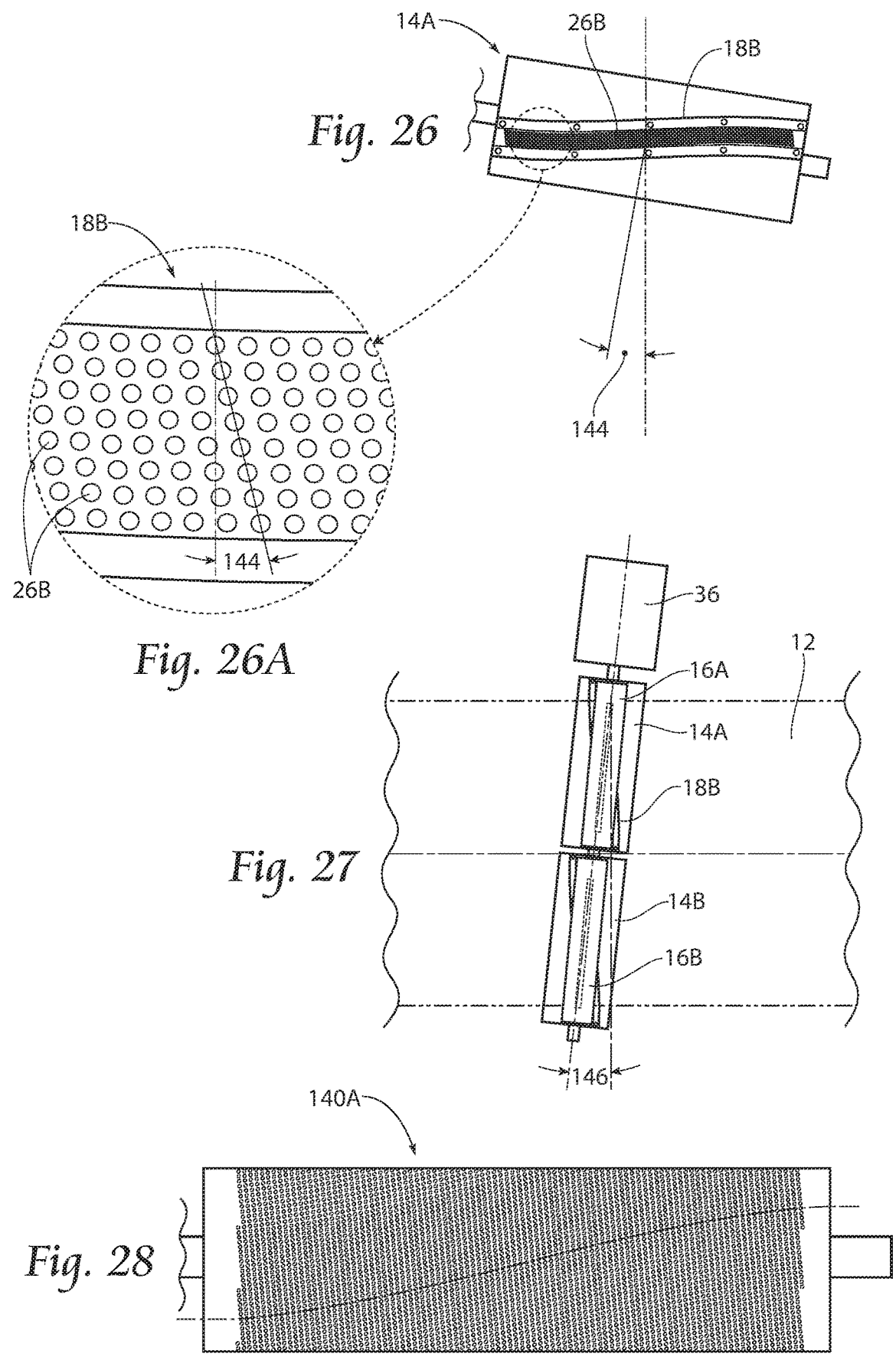

DUAL BONDER

RELATED APPLICATIONS

This application is a continuation-in-part of co-pending U.S. patent application Ser. No. 15/706,150, filed 15 Sep. 2017, which claims the benefit of U.S. Provisional Patent Application Ser. No. 62/395,152, filed 15 Sep. 2016.

BACKGROUND OF THE INVENTION

The present invention relates to disposable hygiene products and more specifically, to methods and apparatuses for processing disposable hygiene products such as baby diapers, adult diapers, disposable undergarments, incontinence devices, sanitary napkins and the like. More specifically, the invention relates to controlling and positioning webs or web segments of a disposable diaper and bonding them. Various types of automatic manufacturing equipment have been developed which produce the desired results with a variety of materials and configurations.

The invention disclosed herein relates to a method for controlling pieces traveling on a production line, specifically a bonding system for bonding a plurality of webs together. Although the description provided relates to diaper manufacturing, the method is easily adaptable to other applications. Although the description provided relates to bonding portions of diapers, the method is easily adaptable to other products, other disposable products, other diaper types and other portions of diapers.

SUMMARY OF THE INVENTION

The current invention is a system and method for producing a disposable undergarment, with the lateral edges of the undergarment bonded by means of an ultrasonic horn. When a blank is formed for an individual undergarment, the lateral edges of opposing edges of the blank will form the seam. When the edges are sealed together, a seam is formed. The individual undergarments may be later separated along the seams.

BRIEF DESCRIPTION OF THE DRAWINGS

FIG. 26 is a top view of another anvil according to the present invention and having a curved anvil insert.

FIG. 26A is an enlarged view of FIG. 26 and showing a bond pattern.

FIG. 27 is a top plan view of webs moving and use of the anvil illustrated in FIG. 26.

FIG. 28 is a top view of another anvil similar to that of FIG. 25, but showing another seal and emboss surface arrangement in which the bond pattern is arranged in a sinusoidal configuration.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
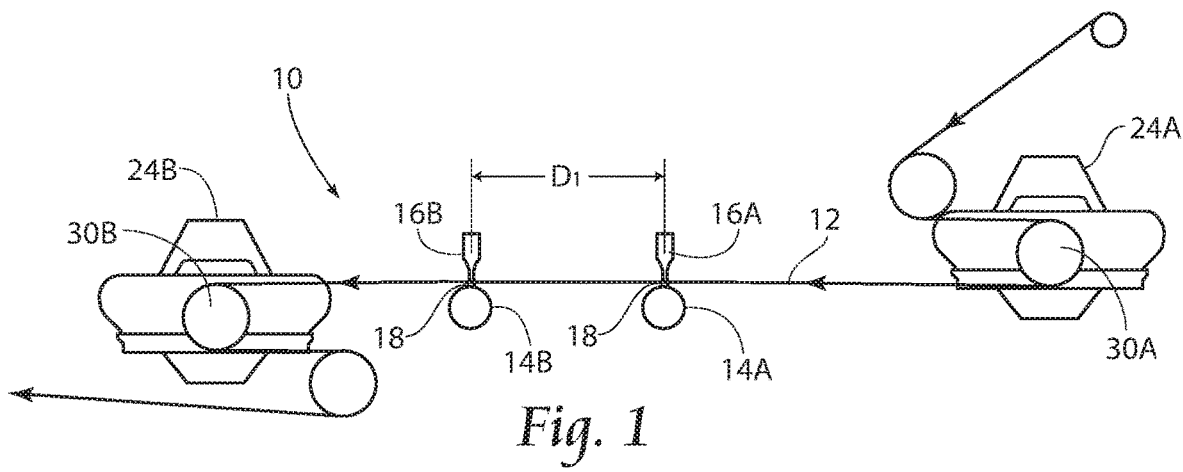
FIG. 1 is a schematic view of a system according the present invention.
Figure 2:
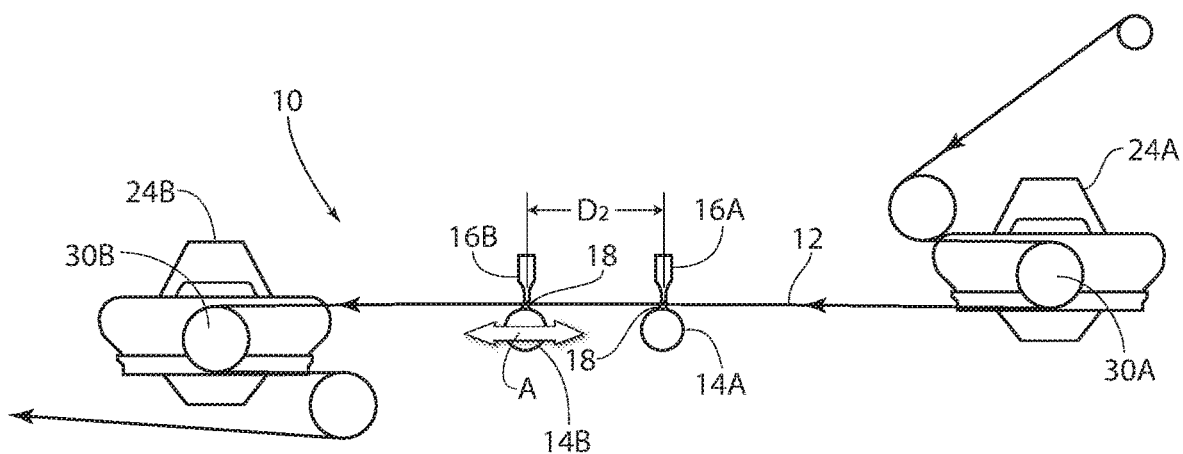
FIG. 2 is a view similar to that of FIG. 1, but showing movement of the component parts to vary the distance between bonds.

With attention to FIGS. 1 and 2, a bonding system 10 is disclosed wherein the positional accuracy of the bonding and quality of the bonding is improved over the prior art. As shown, the system 10 includes an ultrasonic bonder for bonding a plurality webs 12, or a folded web 12 having a front side 12A and a back side 12B. The system 10 includes a first anvil 14A, a second anvil 14B, a first ultrasonic horn 16A, and a second ultrasonic horn 16B. The anvils 14A, 14B are each provided with an anvil insert 18 having a predetermined profile. The first and second anvils 14A, 14B are laterally spaced apart inline and in a machine direction.

The system 10 includes carrying means for carrying the webs 12 so that the webs 12 pass a first gap between the first anvil 14A and the first ultrasonic horn 16A and then a second gap between the second anvil 14B and the second ultrasonic horn 16B. The first and second ultrasonic horns 16A, 16B apply vibration energy to the web 12 simultaneously and in cooperation with a respective anvil 14A, 14B to bond a respective portion of the web 12 that is to be an end portion 20 of an individual finished article (not shown in these views). As mentioned, the first anvil 14A and the first ultrasonic horn 16A are provided inline from the second anvil 14B and the second ultrasonic horn 16B and are spaced apart a predetermined distance d1 that corresponds to the distance between bonds 22. The predetermined distance d1 may be changed to accommodate various sizes of the finished product, since the distance d1 corresponds to the length of the individual article. Accordingly, the length of the individual article may be changed by adjusting the position of the first or second ultrasonic horn 16A, 16B with respect to the other ultrasonic horn 16A, 16B. Moreover, the system 10 includes a device for linear reciprocation of a selected anvil 14A, 14B and ultrasonic horn 16A, 16B relative another anvil 14A, 14B and ultrasonic horn 16A, 16B and to move in the direction of arrow A, (see FIG. 2) and to thereby change the distance d1, d2 between a selected anvil 14A, 14B and horn 16A, 16B and the adjacent anvil 14A, 14B and horn 16A, 16B. Preferably, the selected anvil 14A, 14B and ultrasonic horn is 16A, 16B slidingly mounted to a base structure (not shown), and its movement manually or computer controlled, as understood by one skilled in the art. Since the distance d1, d2 intervals of bonding positions may be changed by changing the position of the first or second ultrasonic horn 16A, 16B, the present system may easily produce individual articles of various sizes. It is to be understood that while the view of FIG. 2 illustrates movement of the second ultrasonic horn 16B, the position of the first ultrasonic horn 16A may also or alternatively be changeable, as required by a specific application.

Figure 7:
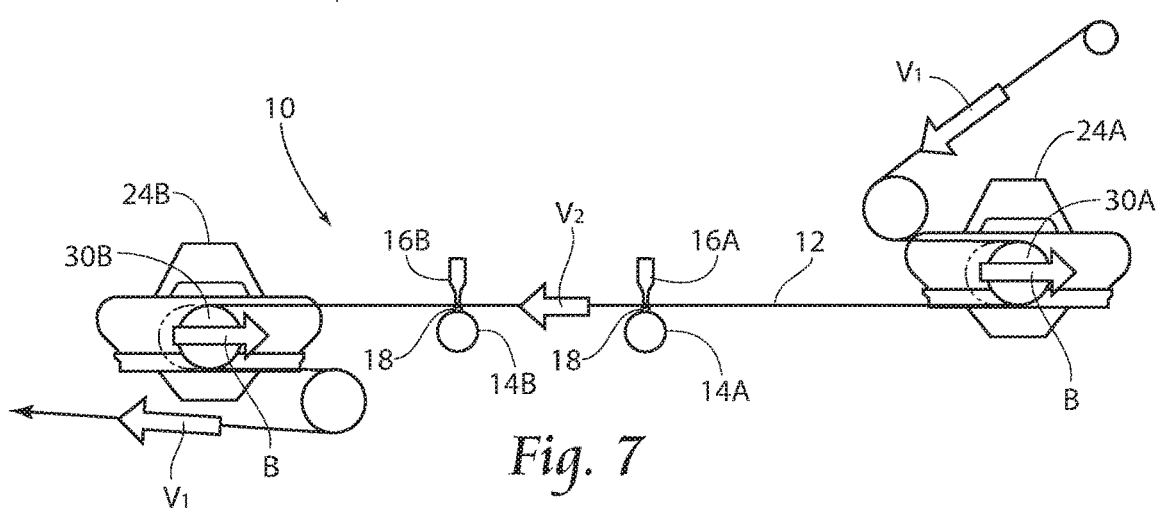
FIG. 7 is a schematic view similar to that of FIG. 6, and showing movement of accumulator rollers to slow the web to a bonding velocity.
Figure 8:
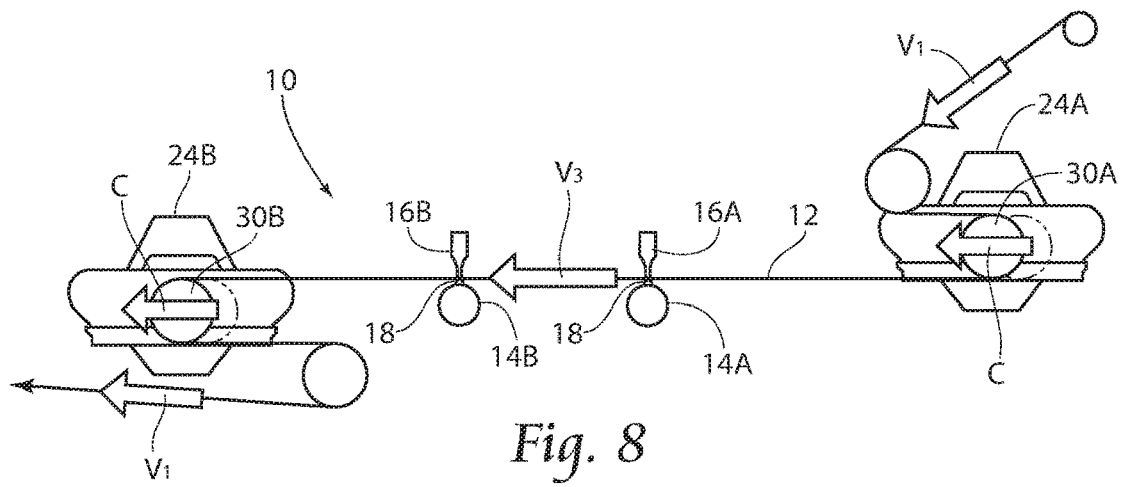
FIG. 8 is a schematic view similar to that of FIGS. 6 and 7, and showing movement of accumulator rollers to increase the velocity web after bonding.
Figure 9:
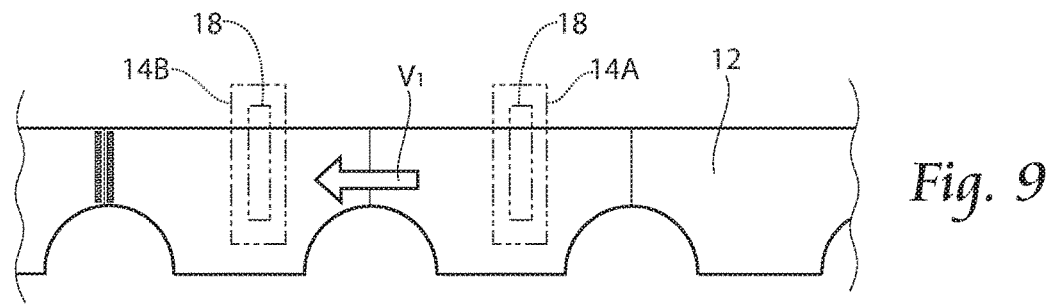
FIG. 9 is a top plan view of webs moving as illustrated in FIG. 6.
Figure 10:
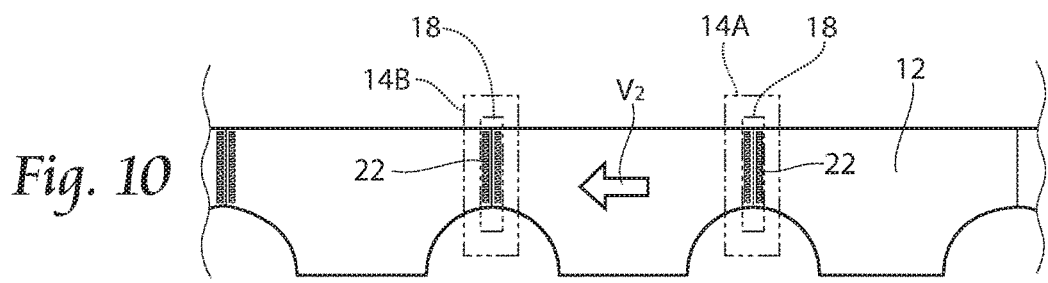
FIG. 10 is a top plan view of webs moving as illustrated in FIG. 7.
Figure 11:
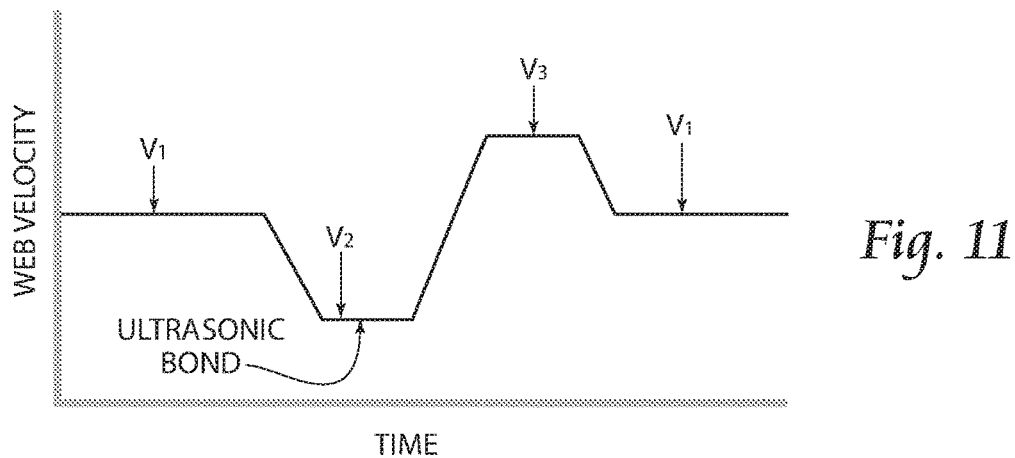
FIG. 11 is a graphic representation of the various web velocities.

With attention to FIGS. 6-11, the present system 10 may be seen to further comprise a velocity-changing device for increasing and decreasing the moving velocity of the web 12. The velocity-changing device preferably includes a first web festoon accumulator 24A having a first accumulator roller 30A, and a second web festoon accumulator 24B having a second accumulator roller 30B. The first web festoon accumulator 24A receives the webs 12 flowing from an upstream side and releases the webs toward the ultrasonic horns 16A, 16B while the second web festoon accumulator 24B receives the webs 12 from the ultrasonic horns 16A, 16B and moves the webs 12 toward a downstream side. The velocity-changing device further includes means for moving the first and second accumulator rollers 30A, 30B in a unison, linear manner to thereby change the velocity V1 of the web 12 received. As seen in FIG. 7, when the first and second accumulator rollers 30A, 30B move in the direction of arrow B, the velocity V1 of the web 12 from the upstream side is moved to second, slower velocity V2, such that the dwell time of the web 12 during the bonding operation is adequate for proper bonding. The anvil rolls 14A, 14B are preferably synchronized such that the device 10 will produce two bonds 22 simultaneously during the slower V2 velocity. Once the web 12 is bonded, the accumulator rollers 30A, 30B move in the direction of arrow C (see FIG. 8) and the webs 12 move at velocity V3 to be ultimately transported by the second web festoon accumulator 24B at the first V1 velocity and in a downstream direction.

Figure 3:
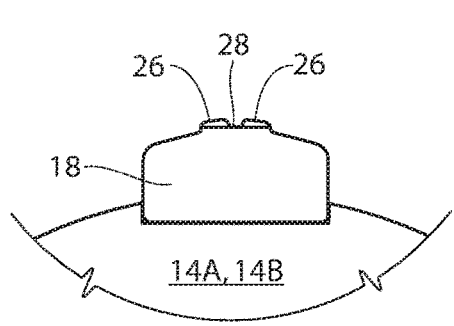
FIG. 3 is an enlarged view of an anvil insert for use with the present system.
Figure 3A:
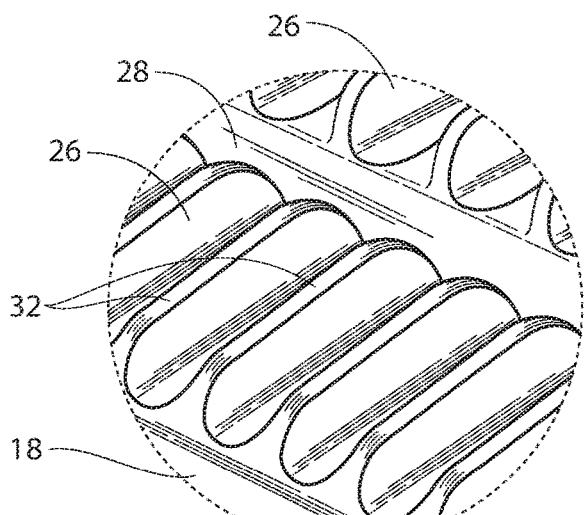
FIG. 3A is an enlarged perspective view of the anvil insert illustrated in FIG. 3.
Figure 4:
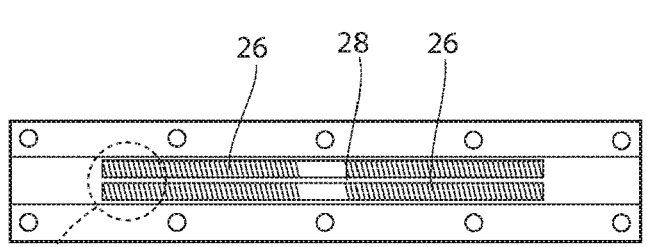
FIG. 4 is a top view of the anvil insert illustrated in FIG. 3.
Figure 4A:
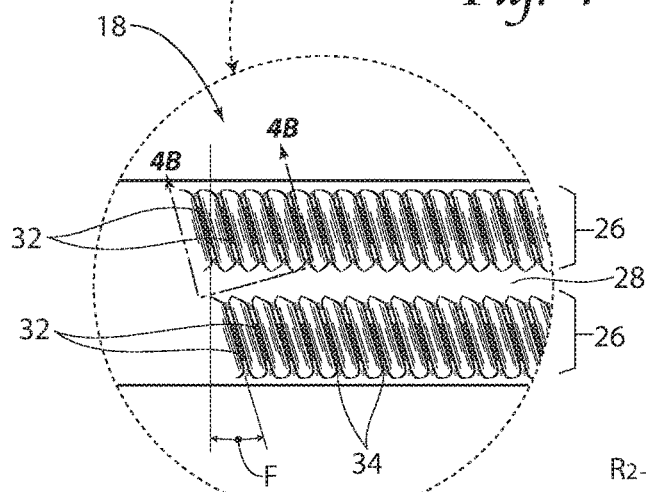
FIG. 4A is an enlarged view of FIG. 4 and showing a bond pattern.
Figure 4B:
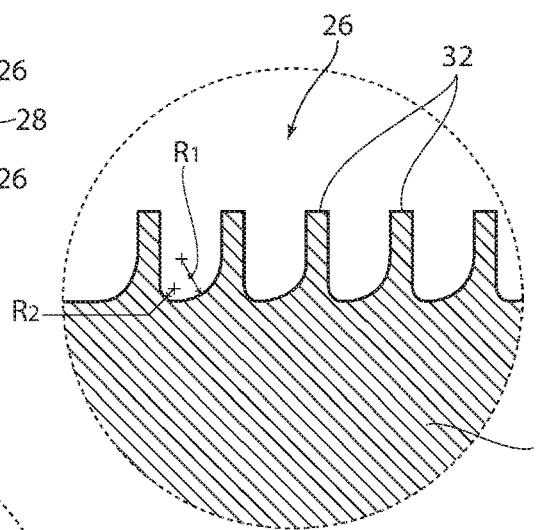
FIG. 4B is a cross sectional view of the anvil insert illustrated in FIG. 4A, and taken along lines 4B-4B thereof.
Figure 4C:
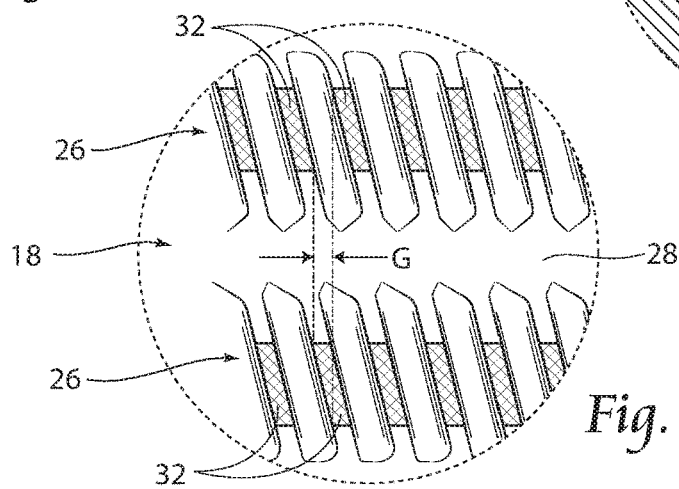
FIG. 4C is an enlarged view of FIG. 4A.

The surfaces of the anvils 14A, 14B used in cooperation with the ultrasonic horns 16A, 16B may preferably include an anvil insert 18, as is shown in FIGS. 3-4C. The anvil insert 18 may include a seal surface, an embossing surface, or a combination thereof. The anvil insert 18 illustrated in these views includes a pair of spaced apart seal surfaces 26 having a recess 28 therebetween and wherein the seal surfaces 26 are provided with a series of canted rectangular patterns or teeth 32 thereon. The canted orientation of the rectangular pattern 32 provides both trailing edge and leading edge coverage in a cross-machine direction. This arrangement allows even wear on the horns 16A, 16B interfacing with the anvils 14A, 14B such that the need to re-grind worn horns 16A, 16B is greatly reduced. Moreover, the cost associated with anvil 14A, 14B assembly is reduced because the anvil 14A, 14B and the insert 18 may be manufactured separately and less material is required. Further, maintenance of the anvil 14A, 14B is easier and less costly since the user requires only a spare insert 18 rather than an entire anvil 14A, 14B when replacement is needed. Typical bond patterns produced by typical anvils (not shown) are not canted and are often merely a series of parallel rectangles (not shown). During use, these typical bond patterns may wear grooves into the surface of the horn 16A, 16B causing downtime for horn 16A, 16B maintenance. The pattern 32 disclosed in FIGS. 4, 4A, 4B and 4C reduces downtime for horn 16A, 16B maintenance. With particular reference to FIGS. 4A and 4B, it may be seen that the canted arrangement of the rectangles or teeth 32, creates a bond pattern that will evenly wear a corresponding ultrasonic horn 16A, 16B. As shown, the edges 34 of adjacent teeth 32 are parallel to one another for facile manufacture. Moreover, the teeth 32 are angled relative to the machine direction at a predetermined angle F (see FIG. 4A) that provides a following tooth 32 to fill in any gaps G (See FIG. 4C) existing between any preceding tooth 32. The view of FIG. 4C illustrates this particular feature in greater detail. Depending on the geometry, such as width of gap between teeth 32 rows, width of gap between teeth 32, and the like, the predetermined angle F may provide full coverage of the ultrasonic horn 16A, 16B to achieve the goal of even wear. While angling the teeth 32 provides more even wear of the ultrasonic horn 16A, 16B, structural liability of the teeth 32 may increase with the angle F. Structural integrity of the teeth 32 may be increased through the use of various radii between the teeth 32 (see FIG. 4B for example). By varying the radii between the teeth 32 such that each tooth has a small radius R2 on one side and a large radius R1 on the other, individual teeth 32 are more structurally sound and the chance of breaking a tooth 32 is greatly reduced. The anvil insert 18 of these views may be used to simultaneously bond adjacent article end portions 20, while reserving a boundary between the sealed end portions for a later severing operation.

Figure 12:
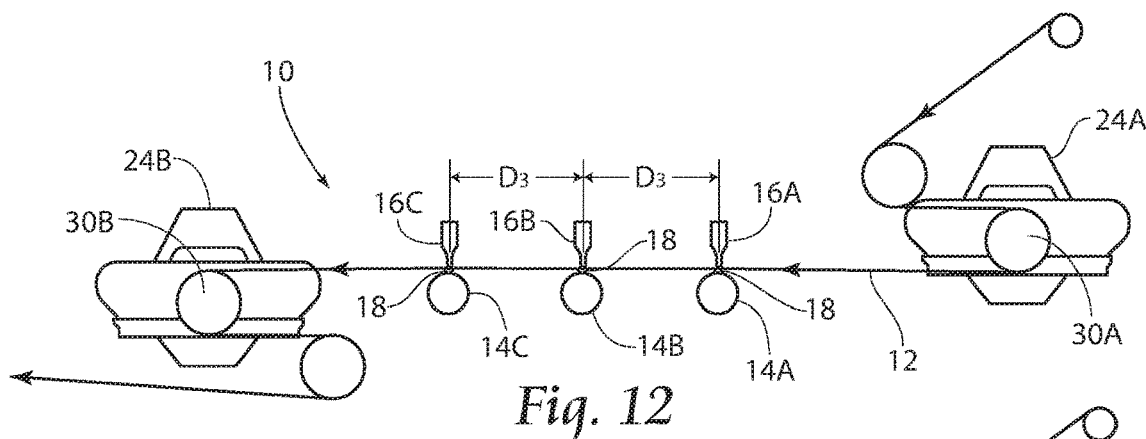
FIG. 12 is a view similar to that of FIG. 1, but showing three anvils and ultrasonic horns.
Figure 13:
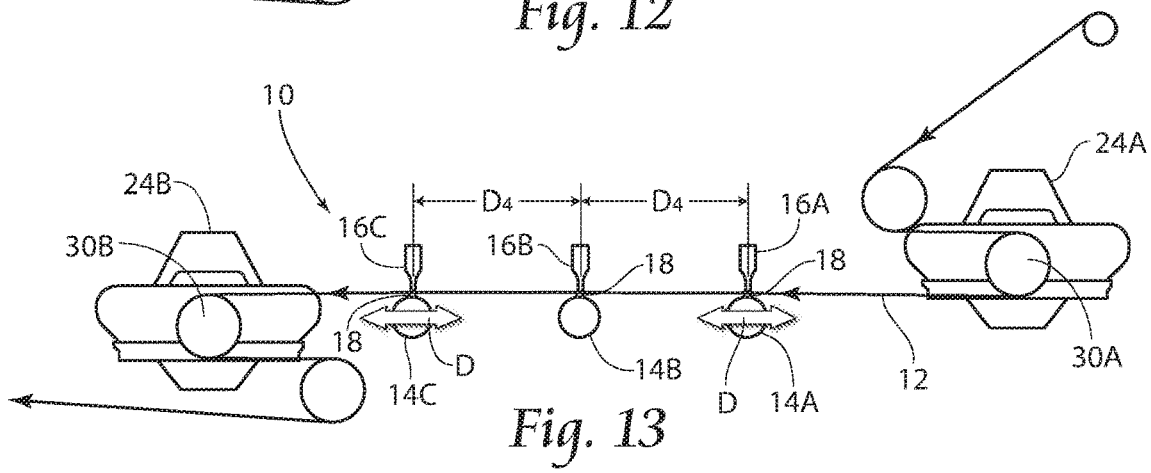
FIG. 13 is a view similar to that of FIG. 12, but showing movement of the component parts to vary the distance between bonds.

With attention to FIGS. 12-15, it may be seen that a bonding system 10 according to the present invention may include a first anvil 14A, a second anvil 14B, a third anvil 14C, a first ultrasonic horn 16A, a second ultrasonic horn 16B, and a third ultrasonic horn 16C. The anvils 14A, 14B, 14C may be each provided with an anvil insert 18 having a predetermined profile, as described above. The anvils 14A, 14B, 14C are laterally spaced apart inline and in a machine direction. As in the previous embodiment, the ultrasonic horns 16A, 16B, 16C apply vibration energy to the web 12 simultaneously and in cooperation with a respective anvil 14A, 14B, 14C to bond a respective portion of the web 12 that is to be an end portion 20 of an individual finished article (not shown in these views). As previously described, the first anvil 14A and the first ultrasonic horn 16A are provided inline from the second anvil 14B and the second ultrasonic horn 16B, with the third anvil 14C and the third ultrasonic horn 16C provided inline from the second anvil 14B and the second ultrasonic horn 16B. The anvils 14A, 14B, 14C with the corresponding horns 16A, 16B, 16C are spaced apart a predetermined distance d3 that corresponds to the distance between bonds 22. The predetermined distance d3 may be changed to accommodate various sizes of the finished product, since the distance d3 corresponds to the length of the individual article. Accordingly, the length of the individual article may be changed by adjusting the position of the first, second, or third ultrasonic horn 16A, 16B, 16C with respect to any other ultrasonic horn 6A, 16B, 16C. Moreover, the system 10 includes a device for linear reciprocation of a selected anvil 14A, 14B, 14C and ultrasonic horn 16A, 16B, 16C relative to another anvil 14A, 14B, 14C and ultrasonic horn 16A, 16B, 16C and to move in the direction of arrow D, (see FIG. 13) and to thereby change the distance d3, d4 between a selected anvil 14A, 14B, 14C and horn 16A, 16B, 16C and the adjacent anvil 114A, 14B, 14C and horn 16A, 16B, 16C. As in the previously described arrangement, a selected anvil 14A, 14B, 14C and ultrasonic horn is 16A, 16B, 16C is preferably slidingly mounted to a base structure (not shown), and the movement manually or computer controlled, as understood by one skilled in the art. Since the distance d3, d4 intervals of bonding positions may be changed by changing the position of the first, second, or third ultrasonic horn 16A, 16B, 16C the present system may easily produce individual articles of various sizes. It is to be understood that while the views of FIGS. 12 and 13 illustrate movement of the first and third ultrasonic horns 16A, 16C, the position of the second ultrasonic horn 16B may also or alternatively be changeable, as required by a specific application. Moreover, the bonding system 10 may include any combination of fixed and moveable ultrasonic horns 16A, 16B, 16C, such as, but not limited to: one fixed ultrasonic horn, with two movable ultrasonic horns; two fixed ultrasonic horns and one movable ultrasonic horn; three fixed ultrasonic horns; and three movable ultrasonic horns, by way of non-limiting example.

Figure 14:
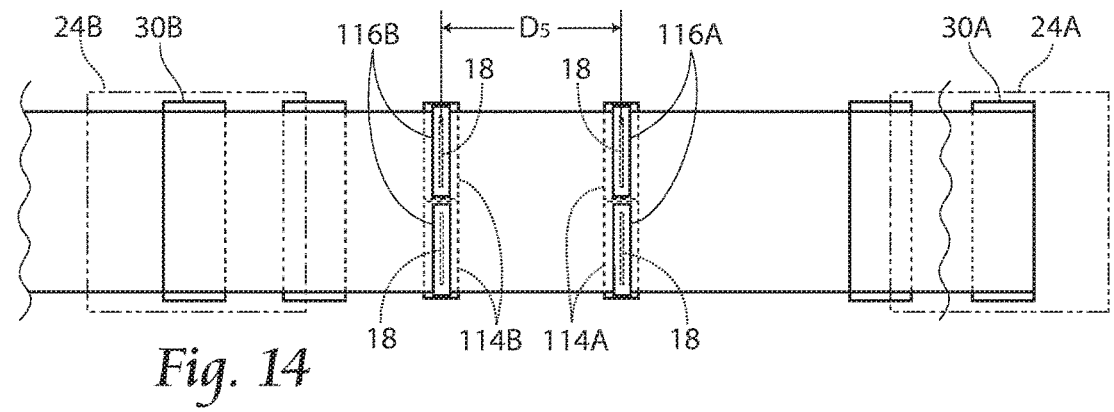
FIG. 14 is a top plan view showing paired anvils and ultrasonic horns.
Figure 15:
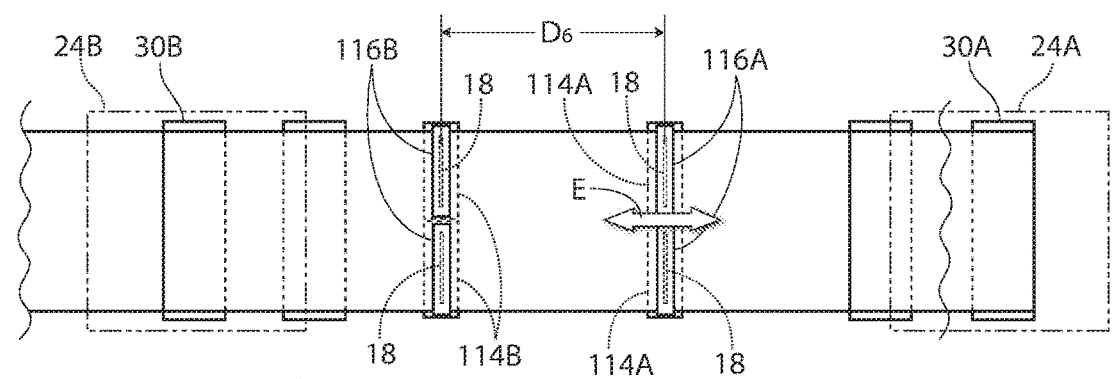
FIG. 15 is a view similar to that of FIG. 14, but showing movement of the component parts to vary the distance between bonds.

FIGS. 14 and 15 illustrate another arrangement of anvils and ultrasonic horns. In these views anvil pairs 114A, 114B are utilized rather that the single anvils 14A, 14B, 14C illustrated in previous views. Moreover, ultrasonic horn pairs 116A, 116B correspond to and cooperate with the anvil pairs 114A, 114B.

Figure 16:
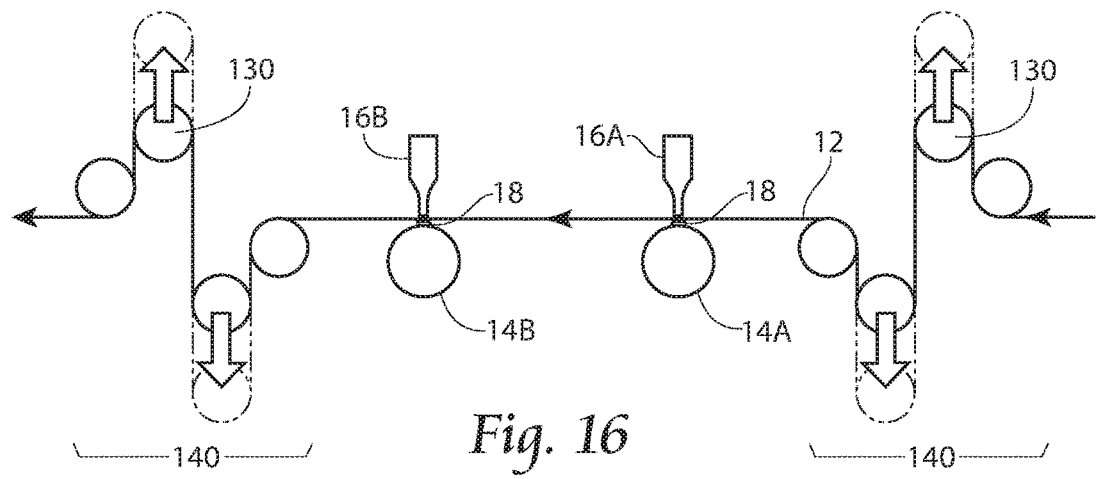
FIG. 16 is a view similar to that of FIGS. 1, 6, and 7 but showing an accumulator series.
Figure 17:
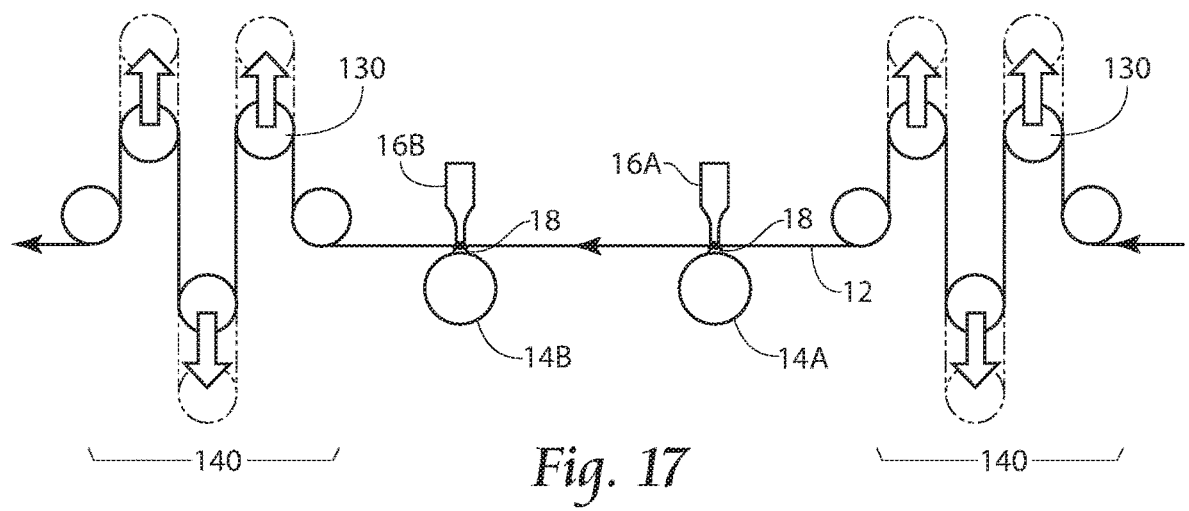
FIG. 17 is a view similar to that of FIGS. 1, 6, 7 and 16 but showing another alternative arrangement for the accumulator series.

FIGS. 16 and 17 illustrate an alternative arrangement and showing a vertical accumulator series 140 rather than the web festoon accumulator 24A, 24B and accumulator rollers 30A, 30B arrangement previously described. As shown, the accumulator series 140 may include any number of roll assemblies 130. It is to be understood that while specific numbers and arrangements of assemblies 130 are shown in the Figures, any number and arrangement of roll assemblies 130 may be envisioned without departing from the invention. Moreover, while not specifically shown, it is to be understood that the accumulator series 140 shown in FIGS. 16 and 17 may be used with any of the anvils 14A, 14B, 14C and ultrasonic horns 16A, 16B, 16C described and Illustrated in previous views.

Figure 18:
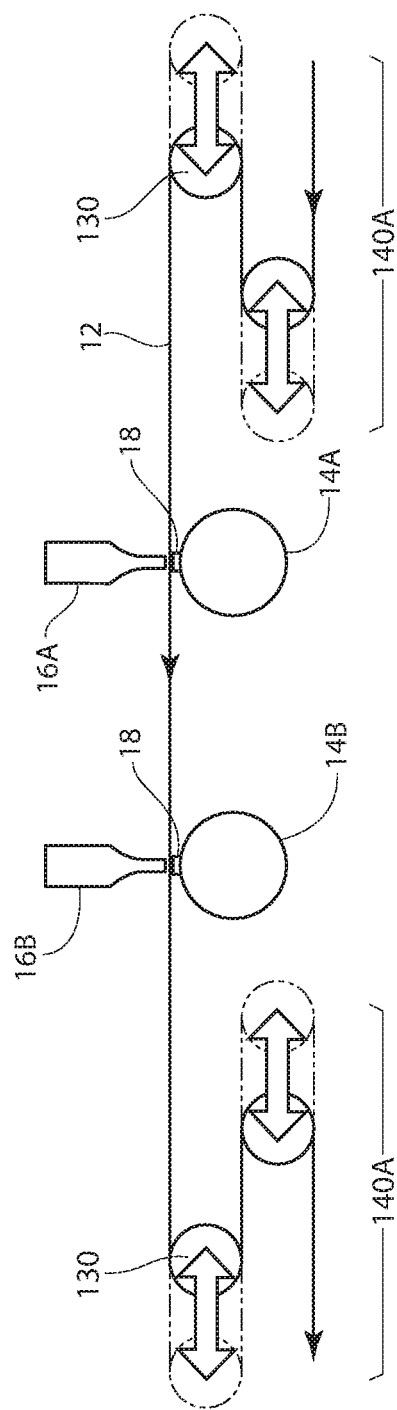
FIG. 18 is a view similar to that of FIGS. 1, 6, 7, 16 and 17 but showing another alternative arrangement for the accumulator series.
Figure 19:
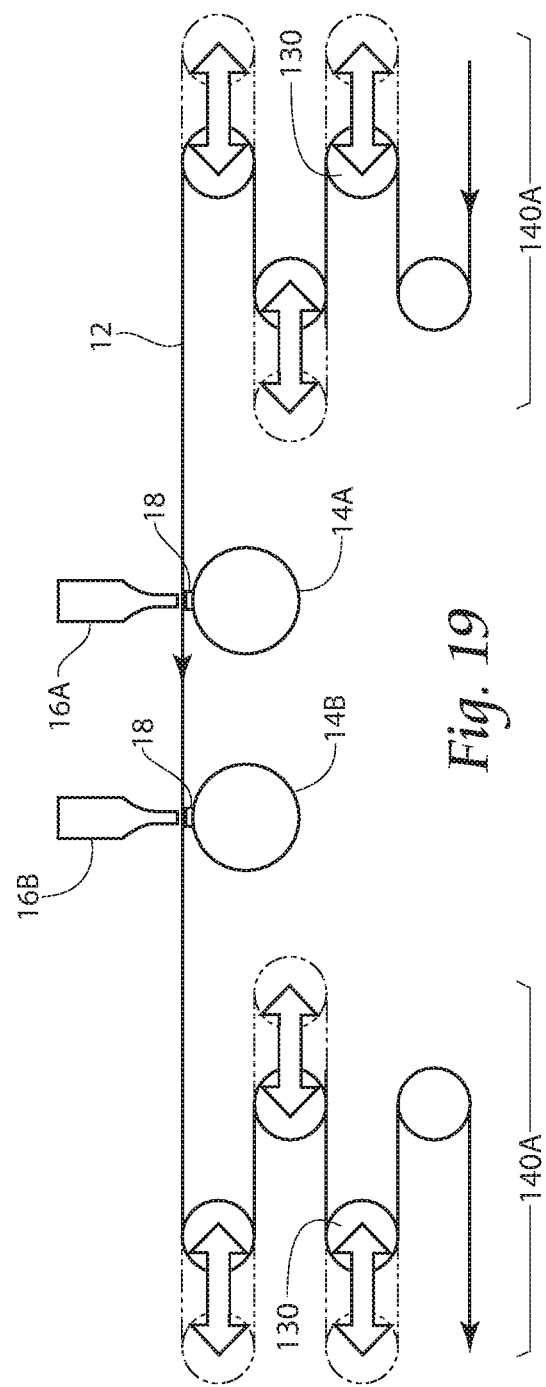
FIG. 19 is a view similar to that of FIGS. 1, 6, 7, 16, 17 and 18 but showing another alternative arrangement for the accumulator series.

FIGS. 18 and 19 illustrate an alternative arrangement similar to that of FIGS. 16 and 17 but showing a horizontal accumulator series 140A. As shown, the accumulator series 140A may include any number of roll assemblies 130. As in the arrangements shown n FIGS. 16 and 17, it is to be understood that the specific number and arrangement of assemblies 130 shown in the Figures should not be considered limiting, and any number and arrangement of roll assemblies 130 may be envisioned without departing from the invention. Moreover, while not specifically shown, it is to be understood that accumulator series 140A shown in FIGS. 18 and 19 may be used with any of the anvils 14A, 14B, 14C and ultrasonic horns 16A, 16B, 16C described and illustrated in previous views.

Figure 20:
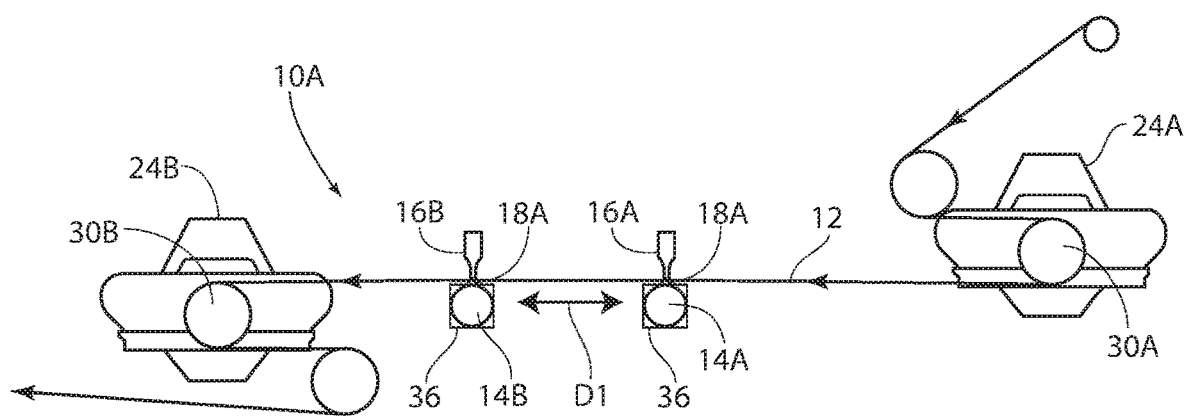
FIG. 20 is a view similar to that of FIGS. 1, 6, 7, 16, 17, 18 and 19 but showing servo motor driven anvils.
Figure 21:
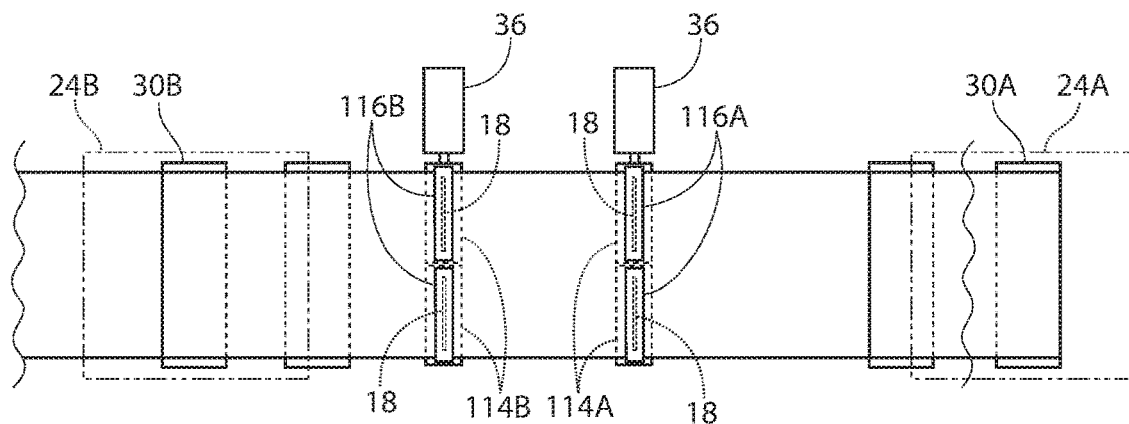
FIG. 21 is a top plan view of the arrangement illustrated in FIG. 20 and showing paired servo driven anvils.
Figure 22:
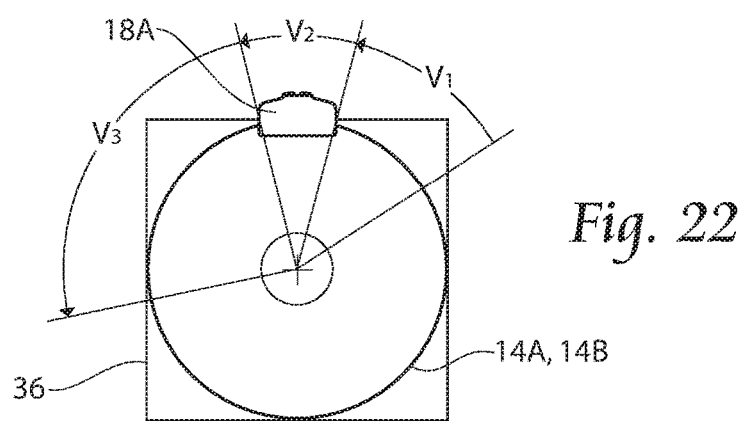
FIG. 22 is an end view of a servo driven anvil and showing various rotational velocity employed during use.

With attention to FIGS. 20 and 21, another bonding system 10A may be seen. As shown, and similar to the system described with reference to FIGS. 1 and 2, system 10 includes an ultrasonic bonder for bonding a plurality webs 12, or a folded web 12. As in the previously described system, the system 10A shown in these views includes a first anvil 14A, a second anvil 14B, a first ultrasonic horn 16A, and a second ultrasonic horn 16B. The anvils 14A, 14B are each provided with an anvil insert 18A having a predetermined profile. The first and second anvils 14A, 14B are laterally spaced apart inline and in a machine direction. The anvils 14A, 14B seen in views are each further provided with a servo motor 36 such that the anvils 14A, 14B may be servo motor driven. As seen in FIG. 22, the servo motor 36 functions to vary the revolution speed of the anvils 14A, 14B. The speed may be varied to thereby influence the dwell time of the anvil insert 18A against the web 12. For example, and as shown in FIG. 22, the revolution speed of the anvils 14A, 14B is varied such that, the revolution speed V1 of the anvils 14A, 14B from the upstream side may be slowed to second, slower velocity V2, such that the dwell time of the web 12 during the bonding operation is adequate for proper bonding. The anvils 14A, 14B are preferably synchronized such that the device 10A will produce two bonds 22 simultaneously during the slower V2 velocity. Once the web 12 is bonded, the anvils 14A, 14B accelerate to velocity V3 to be rotated back to the first V1 velocity, and in a downstream direction.

Figure 5:
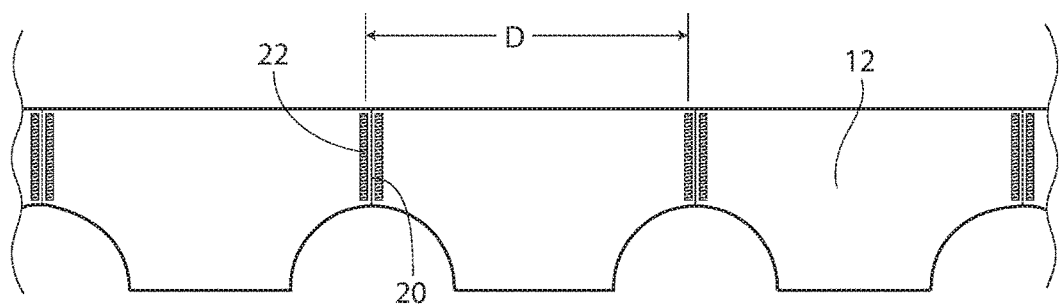
FIG. 5 is a top plan view showing a web with spaced apart bonds.
Figure 6:
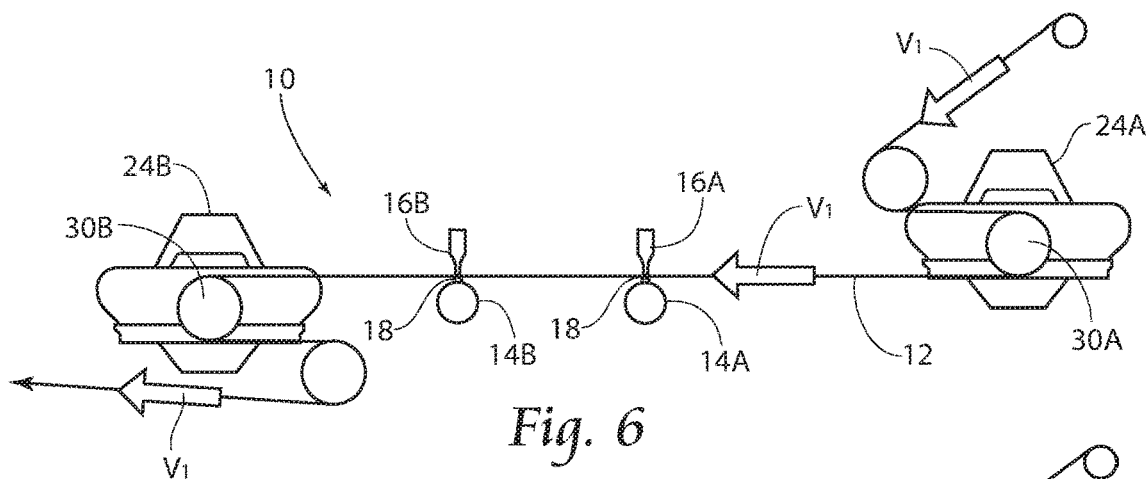
FIG. 6 is a schematic view similar to that of FIG. 1, and showing webs moving at a non-bonding velocity.
Figure 6A:
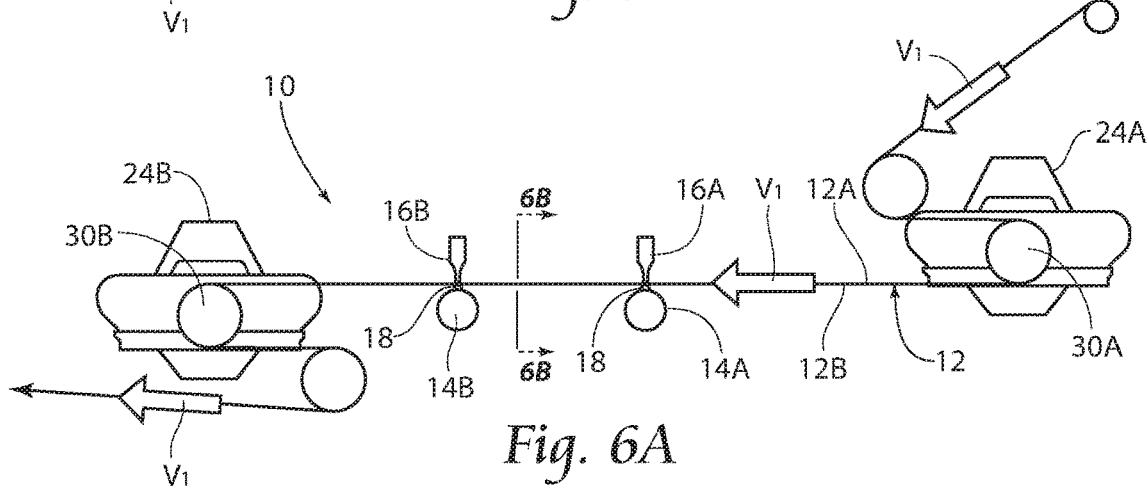
FIG. 6A is a view similar to that of FIG. 6, but showing a front side and a back side of a folded web.
Figure 6B:
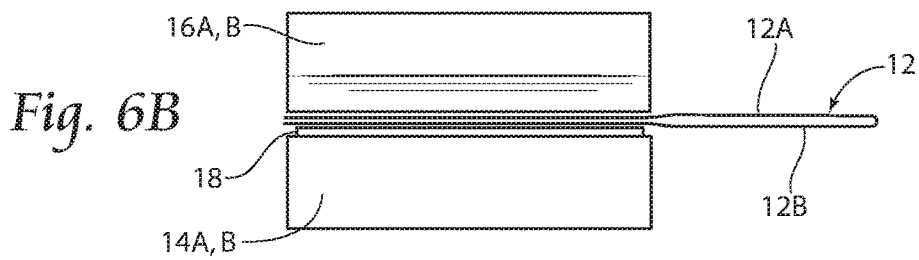
FIG. 6B is a cross sectional view taken along lines 6B-6B of FIG. 6A, and showing a back side adjacent an anvil and a front side adjacent a horn.

As in the previous embodiment, the system 10A shown in these views includes carrying means for carrying the webs 12 so that the webs 12 pass a first gap between the first anvil 14A and the first ultrasonic horn 16A and then a second gap between the second anvil 14B and the second ultrasonic horn 16B. The first and second ultrasonic horns 16A, 16B apply vibration energy to the web 12 simultaneously and in cooperation with a respective anvil 14A, 14B to bond a respective portion of the web 12 that is to be an end portion 20 (see FIG. 5) of an individual finished article (not shown in these views). As mentioned, the first anvil 14A and the first ultrasonic horn 16A are provided inline from the second anvil 14B and the second ultrasonic horn 16B and are spaced apart a predetermined distance d1 that corresponds to the distance between bonds 22. The predetermined distance d1 may be changed to accommodate various sizes of the finished product, since the distance d1 corresponds to the length of the individual article. Accordingly, the length of the individual article may be changed by adjusting the position of the first or second ultrasonic horn 16A, 16B with respect to the other ultrasonic horn 16A, 16B.

Figure 23:
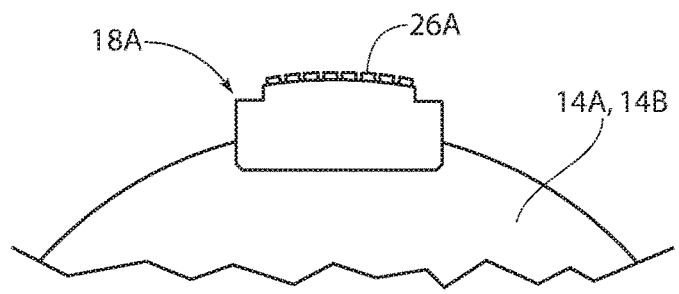
FIG. 23 is an enlarged view of an anvil insert for use with the present system, similar to that of FIG. 3, but showing another seal and emboss surface arrangement.
Figure 24:
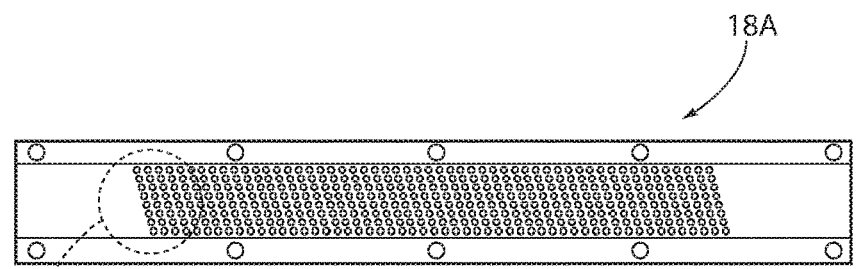
FIG. 24 is a top view of the anvil insert illustrated in FIG. 23.
Figure 24A:
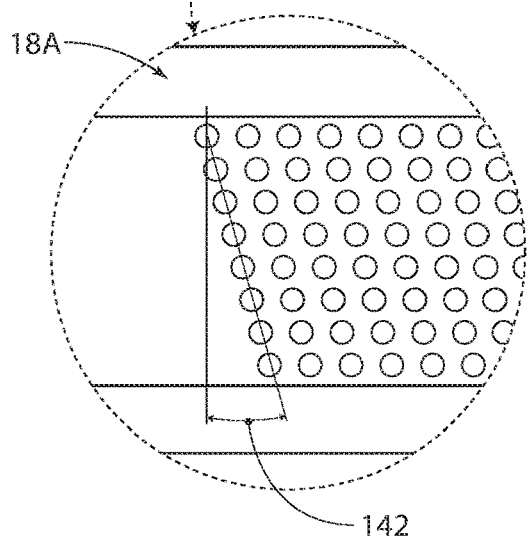
FIG. 24A is an enlarged view of FIG. 24 and showing a bond pattern.
Figure 25:
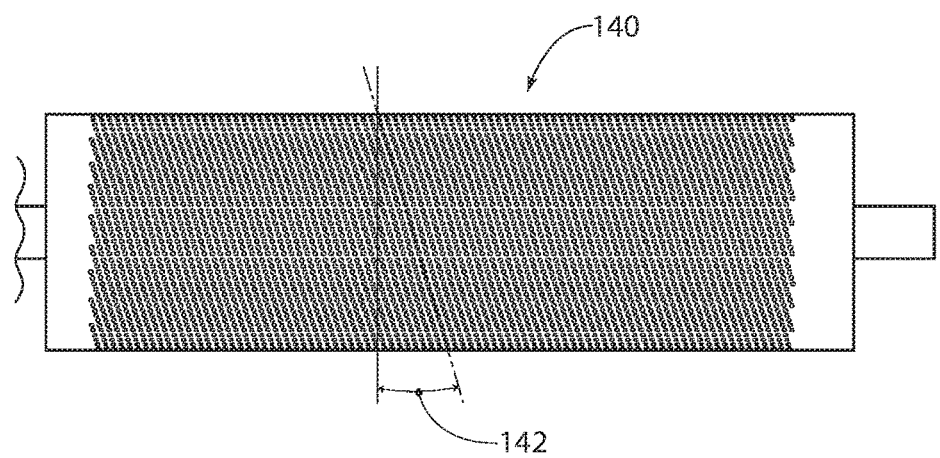
FIG. 25 is a top view of another anvil according to the present invention in which the surface of the anvil includes a seal and emboss surface arrangement.

As in the previous embodiment, the surfaces of the anvils 14A, 14B used in cooperation with the ultrasonic horns 16A, 16B may include an anvil insert 18A, as is shown in FIGS. 23-24A. The anvil insert 18A may include a seal surface, an embossing surface, or a combination thereof. The anvil insert 18A illustrated in these views includes a seal surface having a plurality of raised seal areas 26A and wherein the seal areas 26A are arranged in a pattern that is canted from the machine direction in an angle 142 (see FIGS. 24, 24A). Alternatively, and as seen in FIG. 25, the pattern shown in FIGS. 24, 24A may be applied to the entire anvil 140.

With reference to FIGS. 26-27, it may be seen that the surfaces of the anvils 14A, 14B may include another anvil insert 18B. As shown, and similar to the views of FIGS. 23-24A, the seal surface of these views includes a plurality of raised seal areas 26B which are arranged in a pattern having an angle 144 (see FIG. 26A) relative to the anvil 14A, 14B. The anvil insert 18B is further curved in a helical configuration. As seen in FIG. 27, the angle 144 of the seal area 26B pattern shown in FIG. 26A may be applied (inversely) to the entire unit (horn 16A, 16B and servo-driven anvil roll 14A, 14B) such that the angled seal surface 26B pattern is parallel to the machine direction when the horn 16A, 16B and servo-driven anvil roll 14A, 14B are canted in the cross direction by the inverse angle 146. Alternatively, and as seen in FIG. 28, the seal area 26B pattern shown in FIGS. 25-27 may be applied to the surface of the entire anvil 140A in a helical pattern. As in the arrangement of FIGS. 26-27, the seal surface 26B pattern of anvil 140A is also parallel to the machine direction when the horn 16A, 16B and servo-driven anvil roll 140A is canted in the cross direction by the inverse angle 146 (see FIG. 27). By canting the horn 16A, 16B and servo-driven anvil roll 140A in the angle 146 seen in FIG. 27 the pattern on the anvil 140A is applied in a parallel fashion of the web 12.

The arrangements shown in the views of FIGS. 26-28 increase the anvil 14A, 140A dwell time against the web 12 during bond formation and optimizes the force and power of the bond action. The angle 146 of the horn 16A, 16B and anvil 14A, 140A relative to the angle 144 of the seal surface 26B pattern increases the web 12 leading edge bond. The arrangement increases the typical time that the anvil 140A interacts with the horn 16A, 16B. Moreover, the arrangement minimizes certain known issues with consistent intermittent bond strength, such as spikes in power and weak leading edge bonds. The anvil and horn angle 146 in relation to the running web 12, along with the helical pattern of the seal surface 26B pattern produce a bond that is perpendicular to the machine direction. The arrangement of the helical pattern on the anvil insert 26B and anvil 140A, along with the canted orientation of the anvil 14A, 14B, 140A and horn 16A, 16B relative the machine direction results in less area under the horn 16A, 16B at any point in the bond thereby allowing the potential for higher bond forces. The anvil 14A, 14B, 140A and horn 16A, 16B canted relative the machine direction may preferably be in the range of 5-15°

The angled orientation of the seal surface 26B pattern improves bond coverage in a cross-machine direction and further allows even wear on the horns 16A, 16B interfacing with the anvils 14A, 14B, 140 such that the need to re-grind worn horns 16A, 16B is greatly reduced. As mentioned, typical bond patterns produced by typical anvils (not shown) are not canted and are often merely a series of parallel rectangles (not shown). During use, these typical bond patterns may wear grooves into the surface of the horn 16A, 16B causing downtime for horn 16A, 16B maintenance. The patterns 32 disclosed in FIGS. 24, 25, 26 and 28 reduce downtime for horn 16A, 16B maintenance. The anvil insert 18 in the views of FIGS. 24 and 26 may be used to simultaneously bond adjacent article end portions 20, while reserving a boundary between the sealed end portions for a later severing operation.

It is to be understood that the anvils 14A, 14B, 140A, 140B described above may be utilized singly or in pairs as illustrated, for example in FIG. 27. Moreover, ultrasonic horns 16A, 16B may be paired correspond to and cooperate with paired anvils 14A, 14B, 140A, 140B.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. A bonding system for bonding webs including:
 a first anvil and a corresponding first ultrasonic horn;
 a second anvil and a corresponding second ultrasonic horn, wherein each of the first anvil and the second anvil includes a seal surface having a predetermined profile;
 wherein said first anvil and the second anvil are laterally spaced apart inline and in a machine direction;
 wherein said first anvil and said second anvil are each provided with a respective servo motor configured to rotate said respective anvil at a controlled speed; and
 wherein rotation of said first anvil is controlled relative to rotation of said second anvil via operation of said respective servo motors.

2. The system of claim 1 wherein said seal surface of each of the first anvil and the second anvil comprises an anvil insert having a predetermined seal surface pattern.

3. The system of claim 2 wherein said seal surface pattern is a helical pattern.

4. The system of claim 1 wherein said seal surface of each of the first anvil and the second anvil is arranged in a helical pattern.

5. The system of claim 1 wherein rotation of said first anvil is synchronized with rotation of said second anvil via operation of said respective servo motors.

6. The system of claim 5 wherein a rotational velocity of said first anvil and said second anvil is slowed from a first velocity to a second velocity during bonding of said webs by said first anvil and said corresponding first ultrasonic horn and by said second anvil and said corresponding second ultrasonic horn.

7. The system of claim 6 wherein two bonds are formed simultaneously on said webs by interaction between said first anvil and said corresponding first ultrasonic horn and by interaction between said second anvil and said corresponding second ultrasonic horn.

8. The system of claim 6 wherein said rotational velocity of said first anvil and said second anvil is sped up to a third velocity from said second velocity upon bonding of said webs.

9. A method for bonding webs via operation of a bonding system, the method comprising:
- providing a first anvil and a corresponding first ultrasonic horn;
- providing a second anvil and a corresponding second ultrasonic horn, the first anvil and the second anvil being laterally spaced apart in-line and in a machine direction; and
- bonding the webs at locations corresponding to the first anvil and first ultrasonic horn and to the second anvil and second ultrasonic horn;
- wherein bonding the webs further comprises controlling a rotational speed of each of the first anvil and the second anvil via operation of a first servo motor and a second servo motor operatively coupled thereto; and
- wherein, in controlling the rotational speed of the first and second anvils, the first and second servo motors operate to control the rotational speed of the first anvil relative to the rotational speed of the second anvil.

10. The method of claim 9 wherein the first and second servo motors operate to synchronize the rotational speed of the first anvil with the rotational speed of the second anvil.

11. The method of claim 9 wherein a rotational velocity of the first anvil and the second anvil is slowed from a first velocity to a second velocity during bonding of the webs by the first anvil and the corresponding first ultrasonic horn and by the second anvil and the corresponding second ultrasonic horn.

12. The method of claim 11 wherein two bonds are formed simultaneously on the webs by interaction between the first anvil and the corresponding first ultrasonic horn and by interaction between the second anvil and the corresponding second ultrasonic horn.

13. The method of claim 11 wherein the rotational velocity of the first anvil and the second anvil is sped up to a third velocity from the second velocity by the respective first and second servo motors upon bonding of the webs.

14. The method of claim 9 further comprising varying the in-line spacing between the first anvil and the second anvil to adjust a position of bonds formed on the webs, so as to control a length of an article produced from the webs.

* * * * *